(12) United States Patent
Tersigni

(10) Patent No.: US 8,197,471 B1
(45) Date of Patent: Jun. 12, 2012

(54) CORE-EXCITED NANOPARTICLES AND METHODS OF THEIR USE IN THE DIAGNOSIS AND TREATMENT OF DISEASE

(75) Inventor: Samuel Harry Tersigni, Glen Allen, VA (US)

(73) Assignee: Samuel Harry Tersigni, Alpha, NJ (US)

( * ) Notice: Subject to any disclaimer, the term of this patent is extended or adjusted under 35 U.S.C. 154(b) by 0 days.

(21) Appl. No.: 13/052,951

(22) Filed: Mar. 21, 2011

Related U.S. Application Data

(60) Provisional application No. 61/442,615, filed on Feb. 14, 2011.

(51) Int. Cl.
*A61B 18/04* (2006.01)

(52) U.S. Cl. .......................................... 606/27; 977/904

(58) Field of Classification Search .................... 606/27, 606/34, 41; 977/904
See application file for complete search history.

(56) References Cited

U.S. PATENT DOCUMENTS

| | | | |
|---|---|---|---|
| 3,294,699 A | 12/1966 | Horst | |
| 4,499,005 A | 2/1985 | McColl | |
| 6,530,944 B2 | 3/2003 | West | |
| 6,576,221 B1 * | 6/2003 | Kresse et al. | 424/9.322 |
| 7,074,175 B2 | 7/2006 | Handy | |
| 7,510,555 B2 * | 3/2009 | Kanzius | 606/33 |
| 7,834,331 B2 * | 11/2010 | Ben-Yakar et al. | 250/492.1 |
| 2006/0241585 A1 * | 10/2006 | Silberberg et al. | 606/45 |
| 2007/0292495 A1 * | 12/2007 | Ludwig et al. | 424/450 |
| 2009/0263394 A1 | 10/2009 | Scanlan | |

FOREIGN PATENT DOCUMENTS

| WO | 2007002493 | 1/2007 |
|---|---|---|

OTHER PUBLICATIONS

Bassett et al., "Prolonged cholestasis and ductopenia following gold salt therapy", Liver Intl., 23:89-93 (2003).

Chang, et al., "Eu2+ Activated long persistent strontium aluminate nano scaled phosphor prepared by precipitation method", J. of Alloys and Compounds, 415:220-224 (2006).

Chen and Zhang, "Using nanoparticles to enable simultaneous radiation and photodynamic therapies for cancer treatment", J. Nanoscience and Nanotechnology, 6:1159-66 (2006).

Chen et al., "Comparative efficiencies of photothermal destruction of malignant cells using antibody-coated silica@Au nanoshells, hollow Au/Ag nanospheres and Au nanorods", Nanotechnology, 20 (42):425104/1-425104/9 (2009).

(Continued)

*Primary Examiner* — Michael Peffley
*Assistant Examiner* — Daniel Fowler
(74) *Attorney, Agent, or Firm* — Pabst Patent Group LLP

(57) ABSTRACT

Core-excited nanoparticle thermotherapy (CENT), is an improved material for use in thermotherapy. The CENT method uses both core-exciting energy (including x-rays) and core-shell nanoparticles, specifically designed to absorb radiation in their core structure, then transfer energy from the core to the shell, to heat the outer shell of the nanoparticle. The heated nanoparticle then heats the surrounding region to a temperature sufficient to detect, affect, damage and/or destroy the targeted cell or material. CENT nanoparticles can be bound to targeting agents that deliver them to the region of the diseased cell.

51 Claims, 5 Drawing Sheets

OTHER PUBLICATIONS

Das et al., "Gadolinium oxide ultranarrow nanorods as multimodal contrast agents for optical and magnetic resonance imaging", Langmuir, 26(11):8959-65 (2010).

El-Kouedi and Foss "Optical Properties of Gold-Silver Nanoparticle Pair Structures", J. Phys. Chem. 104:4031-37 (2000).

El-Sayed, et al., "Surface plasmon resonance scattering and absorption of anti-EGFR antibody conjugated gold nanoparticles in cancer diagnostics: applications in oral cancer", Nanoletters, 5(5):829-834 (2005).

Jessop et al., "A long-term five-year randomized controlled trial of hydroxychloroquine, sodium aurothiomalate, auranofin and penicillamine in the treatment of patients with rheumatoid arthritis", Br J Rheumatol, 37:992-1002 (1998).

Kirui et al, "Gold hybrid nanoparticles for targeted phototherapy and cancer imaging", Nanotechnology,21(10):105105 (2010).

Link and El-Sayed, "Size and Temperature Dependence of the Plasmon Absorption of Colloidal Gold Nanoparticles", J. Phys. Chem. B, 103(21):4212 (1999).

Moses, et al., "Prospects of dense, infrared emitting scintillators", IEEE Trans. Nucl Sci., NS-45, 462-466 (1998).

Pal et al., "Preparation of stable silver and silver-gold bimetallic nanoparticle in W/O microemulsion containing tritonX-100", African Phys. Rev. 1 (Special Issue—Microfluidics) (2007).

Ruoslahti, "Specialization of tumour vasculature", Nat. Rev. Cancer, 2:83-90 (2002).

* cited by examiner

CORE-EXCITED NANOPARTICLES AND METHODS OF THEIR USE IN THE DIAGNOSIS AND TREATMENT OF DISEASE

CROSS REFERENCE TO RELATED APPLICATIONS

This application claims priority to U.S. Ser. No. 61/442,615 filed on Feb. 14, 2011 by Samuel Harry Tersigni, the contents of which is hereby incorporated by reference in its entirety.

FIELD OF THE INVENTION

The present invention is generally in the field of core-shell nanoparticles, especially metal and ceramic core nanoparticles, for use in diagnosis and treatment of disease.

BACKGROUND OF THE INVENTION

Generation of heat in the range of temperature from about 40° C. to about 46° C. (hyperthermia) can cause irreversible damage to diseased cells, whereas normal cells are not similarly affected. Three widely investigated methods for inducing hyperthermia, including radio-frequency waves, magnetic fields and near infrared radiation, have been utilized. As mentioned in U.S. Pat. No. 7,074,175 to Handy, "Hyperthermia may hold promise as a treatment for cancer because it induces instantaneous necrosis (typically called thermo-ablation) and/or a heat-shock response in cells (classical hyperthermia), leading to cell death via a series of biochemical changes within the cell. State-of-the-art systems that employ radio-frequency (RF) hyperthermia, such as annular phased array systems (APAS), attempt to tune E-field energy for regional heating of deep-seated tumors. Such techniques are limited by the heterogeneities of tissue electrical conductivities and that of highly perfuse tissues, leading to the unsolved problems of 'hot spot' phenomena in unintended tissues with concomitant under dosage in the desired areas. These factors make selective heating of specific regions with such E-field dominant systems very difficult."

As further mentioned by Handy et al., "Hyperthermia for cancer treatment using colloidal single domain magnetic suspensions (i.e., magnetic fluids) exposed to RF fields has been recognized for several decades. However, a major problem with magnetic fluid hyperthermia has been the inability to selectively deliver a lethal dose of particles to the tumor cells." Nevertheless, these various approaches to cell-specific hyperthermia are active areas of research. Finally, it should be noted that, in some cases, heating of the local cell environment may be sufficient to kill the targeted cell but not sufficient to raise the temperature of the bulk medium.

Several laboratories have investigated cell-specific nanoparticle-based hyperthermia based on near infrared radiation (NIR). Research includes using techniques of NIR to excite gold nanoparticles and nanoshells as described in U.S. Pat. No. 6,530,944 to West et al. In the '944 patent, after nanoparticles are delivered to a tumor or nearby cancer cells, an external NIR laser of about 800 nm in wavelength is used to excite the gold shell (plasmon mode), to generate the necessary heat. The choice and design of core material shifts the natural plasmon resonance of the gold nanoshell from the 500 nm range (of solid gold nanoparticles) to the 800 nm range. A 800 nm NIR laser is used for optimal transmission through mammalian tissue due to "water windows" for NIR. The essentially energetically inert cores of these nanomaterials in the '944 patent are made of silica and gold sulfide, neither of which absorb x-rays in any significant amount. No example in the '944 patent discusses x-rays, except with respect to the diagnostic embodiments, in which the shell is doped with scintillator material. Such technical approaches are most likely to be effective for cells in a test tube or for surface tumors of the skin. However, NIR is of limited practical clinical value for most cancers because of the inability of safe amounts of NIR to penetrate more than a few centimeters into the human body. The '944 patent also discusses the use of scintillation probes that emit IR and NIR for imaging purposes, but there is no discussion of attempts at therapeutic heat treatment with such an approach.

Further work on evaluating NIR ablation of tumor cells with different types of gold (Au) and silver (Ag) nanoparticle structures has been reported by Chen et al., *Nanotechnology* 20(42), 425104/1-425104/9 2009. Three Au-based nanomaterials (silica core Au nanoshells, hollow Au/Ag nanospheres and Au nanorods) were evaluated for their comparative photothermal efficiencies at killing three types of malignant cells (A549 lung cancer cells, HeLa cervix cancer cells and TCC bladder cancer cells) using a continuous wave (CW) NIR laser. Photo destructive efficiency was evaluated as a function of the number of nanoparticles required to destroy the cancer cells under 808 nm laser wavelength at fixed laser power. Of the three nanomaterials, silica-core gold (Au) nanoshells needed the minimum number of particles to produce effective photo destruction, whereas gold nanorods needed the largest number of particles. Together with the calculated photothermal conversion efficiency, the photothermal efficiency rankings are silica-core Au nanoshells greater than hollow Au/Ag nanospheres greater than Au nanorods.

Delivering the nanoparticle to the vicinity of the targeted cell ("targeting") is of critical importance. Beyond simply injecting the nanoparticles into a region of interest, there are a wide range of targeting methodologies involving tumor cell surface molecules, including the conjugation of antibodies to various therapeutic agents and drugs. The U. S. Food & Drug Administration (FDA) has approved a number of antibody-based cancer therapeutics. The ability to engineer antibodies, fragments, and peptides with altered properties such as antigen binding affinity, molecular architecture, specificity, and valence has enhanced their use in therapies. The advantages of antibody engineering have overcome the limitations of mouse monoclonal antibodies. Cancer immunotherapeutics have made use of advances in the chimerization and humanization of mouse antibodies to reduce immunogenic responses in humans. High affinity human antibodies have also been obtained from transgenic mice that contain many human immunoglobulin genes. In addition, phage display technology, ribosome display, and DNA shuffling have allowed for the discovery of antibody fragments and peptides that have the desirable properties of high affinity and low immunogenicity for use as targeting ligands. All of these advances have made it possible to design an immunotherapy that has a desired antigen binding affinity, specificity, and minimal immune response. In summary, there are several methods of targeting, including monoclonal antibodies (mABs) which are a practical way to carry a lethal agent specifically to the cancer cell and not to normal tissue.

The field of cancer immunotherapy makes use of markers that are expressed or over-expressed on cancer cells in comparison to normal cells. The identification of such markers is ongoing and the choice of a ligand/marker combination is critical to the success of any immunotherapy. Immunotherapy has fallen into several classes: (1) antibodies themselves that target growth receptors, disrupt cytokine pathways, or induce complement or antibody-dependent cytotoxicity; (2) direct arming of an antibody with a toxin, a radio nucleotide, or a cytokine; (3) indirect arming of an antibody by attachment to immunoliposomes used to deliver a toxin or by attachment to an immunological cell effectors (bispecific antibodies). Although armed antibodies have shown more potent tumor activity in clinical trials, there have been unacceptably high levels of toxicity. The disadvantage of therapies that rely on delivery of immunotoxins or radionucleotides (direct and indirect arming) has been that these agents are active at all times. There have been problems with damage to non-tumor cells and toxicity along with delivery challenges. Many immunotherapies have faced challenges with shed markers and delivery to the intended target. Cancer cells commonly shed antigen targets into the blood stream. Many antibody-based therapies are diluted by interaction with shed antigens. In addition, immune complexes can be formed between the immunotherapeutic and the shed antigen, which can lead to dose-limiting toxicities.

Therefore, the state-of-the-art regarding the use of nanoparticle-based cell-specific hyperthermia to treat most disease is such that nanoparticles can be delivered to the targeted cell, but these particles cannot be sufficiently heated to kill cells. The nanoparticles are not efficient producers of thermal energy with the energy sources and energy amounts supplied to them. New methods, involving new nanoparticle designs and energy sources, are needed to enable hyperthermia to be a practical and efficacious treatment method for disease.

It is therefore an object of the present invention to provide nanoparticles which are effective and efficient for use in hyperthermia treatment of diseases and disorders such as cancers, and which can be targeted for even greater specificity.

SUMMARY OF THE INVENTION

Core-excited nanoparticle thermotherapy (CENT), represents a new paradigm in thermotherapy. The CENT method uses both core-excitation energy such as ionizing radiation (including x-rays) and core-shell nanoparticles, preferably formed of metal or ceramic, specifically designed to absorb such radiation in their core structure, then transfer energy from the core to the shell, to heat the outer shell of the nanoparticle. The heated nanoparticle then heats the surrounding region to a temperature sufficient to detect, affect, damage and/or destroy the targeted cell or material. CENT nanoparticles can be bound to targeting agents that deliver them to the region of the diseased cell.

In preferred embodiments, the nanoparticle core material may be any form of strontium aluminate, such as $Sr_aAl_bO_c$, where a, b and c are integers that may vary (e.g., $Sr_4Al_{14}O_{25}$, $SrAl_2O_4$, $SrAl_2O_7$, and $Sr_3Al_2O_6$); any form of strontium aluminate doped with a rare earth element (RaE), $Sr_aAl_bO_c$:RaE, wherein a, b and c are integers that may vary and RaE=Ce, Pr, Nd, Sm, Eu, Tb, Dy, Ho, Er, Tm, or Yb in one or more oxidation states, such as Europium(II)-, Dysprosium(III)-, and Neodymium(III)-doped $Sr_4Al_{14}O_{25}$, $SrAl_2O_4$, $SrAl_2O_7$, and $Sr_3Al_2O_6$; any form of strontium aluminate co-doped with two or more different rare earth elements (RaEs), $Sr_aAl_bO_c$:(RaE)$_2$, wherein a, b and c are integers that may vary and RaE=Ce, Pr, Nd, Sm, Eu, Tb, Dy, Ho, Er, Tm, or Yb in one or more oxidation states, such as strontium aluminate co-doped with Europium(II) and Dysprosium(III) as in $Sr_4Al_{14}O_{25}$:$Eu^{2+}$:$Dy^{3+}$, $SrAl_2O_4$:$Eu^{2+}$:$Dy^{3+}$, $SrAl_2O_7$:$Eu^{2+}$:$Dy^{3+}$, and $Sr_3Al_2O_6$:$Eu^{2+}$:$Dy^{3+}$; and strontium aluminate co-doped with Europium(II) and Neodymium(III) as in $Sr_4Al_{14}O_{25}$:$Eu^{2+}$:$Nd^{3+}$, $SrAl_2O_4$:$Eu^{2+}$:$Nd^{3+}$, $SrAl_2O_7$:$Eu^{2+}$:$Nd^{3+}$, and $Sr_3Al_2O_6$:$Eu^{2+}$:$Nd^{3+}$; any form of rare-earth ion-doped gadolinium oxide or oxysulfide phosphor, $Gd_2O_3$:$RaE^{3+}$ or $Gd_2O_2S$:$RaE^{3+}$, wherein RaE=Ce, Pr, Nd, Sm, Eu, Tb, Dy, Ho, Er, Tm, or Yb; any rare-earth (RaE) ion co-doped alkaline earth aluminate, $xMO+yAl_2O_2$: RaE' RaE, where x and y are integers, and M=Ca, Sr, or Ba, and RaE=Ce, Pr, Nd, Sm, Eu, Tb, Dy, Ho, Er, Tm, or Yb; any rare-earth- or transition-metal-doped metal halide, including, but not limited to, $LaF_3$:$Ce^{3+}$, $LuF_3$:$Ce^{3+}$, $CaF_2$:$Mn^{2+}$, $CaF_2$:$Eu^{2+}$, $BaFBr$:$Eu^{2+}$, $BaFBr$:$Mn^{2+}$, $CaPO_4$:$Mn^{2+}$, $LuI_3$:Ce, $SrI_2$:Eu, $CaI_2$:Eu, $GdI_3$:Ce; or any other suitable material, such as CdS, CdSe, CdTe, $CaWO_4$, ZnS:Cu, TmO, ZnSe:Te, ZnS, ZnO, $TiO_2$, GaN, GaAs, GaP, InAs, InP, $Y_2O_3$, $WO_3$, and $ZrO_2$.

In a preferred embodiment, ionizing radiation, predominantly x-ray radiation, is applied to the nanoparticles consisting of special core material and an energy conducting shell. In theory almost any form of energy can be used to heat the core of the particles. However, the core must be designed to both absorb the excitation energy, then transfer the energy to heat the shell. Other forms of heating the core of the particles include magnetic radiation, infrared or other light, for example, applied with a laser, ultrasound, or radio-frequency. The particles are administered to individuals with cancer or other disease or disorder. In the preferred embodiment a nanoparticle with a core material comprising a significant portion of x-ray absorbing species allows transfer of absorbed energy to the particle shell. The core and the shell are designed to simultaneously optimize the internal molecular energy flow such that x-ray (or gamma ray) energy received in the core is converted to heat emission from the shell. In the case where the energy transfer between core and shell is via electromagnetic radiation, the core is designed so that its x-ray excited emission spectrum overlaps the absorption spectrum of the shell. The physical and optical parameters of the shell are matched to the design capabilities of the core material. The emission spectrum of the core material must significantly overlap the absorption spectrum of the shell material.

Since x-ray radiation is ionizing of tissue and damaging to the body, the minimum amount of x-ray exposure to the patient is most preferred. It is important to maximize the amount of energy transferred from the core into the shell. Materials exhibiting X-ray excited scintillation luminescence or persistent luminescence (long-lived phosphors) have been shown to have emission in the 100 nm to 6000 nm range, which overlaps the region of the spectrum needed to heat gold nanoshells. Other metals, such as silver, platinum and palladium, or mixtures thereof, also serve as effective nanoshells for heating via plasmon absorption.

In a further embodiment, the nanoparticles employ chemical targeting agents to deliver them to the target cell or tissue, either in vivo or in vitro. In the preferred embodiment, the nanoparticles are bound to a targeting antibody which can further participate, either in vivo or in vitro, in antigen-antibody binding or binding to the targeted cell.

In another embodiment, heat-catalyzed functional agents (HCFAs) are bound to or associated with the nanoparticle shell or a targeting support film. HCFAs can be any therapeutic, prophylactic, or diagnostic agent which is bound to the shell or targeting support film of the nanoparticle and is released (or reacted) upon heating of the shell. In a preferred embodiment, the HCFA is an antineoplastic agent.

This technology provides practical, cost-effective methods and nanomaterial compositions for diagnosis and hyperthermia treatment of disease or disorders. The technology should be effective to treat disease that has spread throughout the body, such as metastatic cancers (known as stage IV, in the case of cancer), even when the disease is in such small amounts or locations in the body that it is not detectable. The materials and methods can also be used for imaging, with detection resulting from either the x-ray absorption or the generation of heat. The technology is practical, effective, and non-invasive, with minimal side-effects, that should be usable with existing medical hardware now widely deployed in hospitals around the world.

BRIEF DESCRIPTION OF THE DRAWINGS

FIG. 4a, BaFBr:Eu2+, Mn2+ (20 nm diameter), FIG. 4b, $LaF_3$:$Ce^{3+}$ (15 nm diameter). (Taken from Chen and Zhang, *J. Nanoscience and Nanotechnology* 6, 1159-1166, 2006.)

DETAILED DESCRIPTION OF THE INVENTIONS

Figure 1:
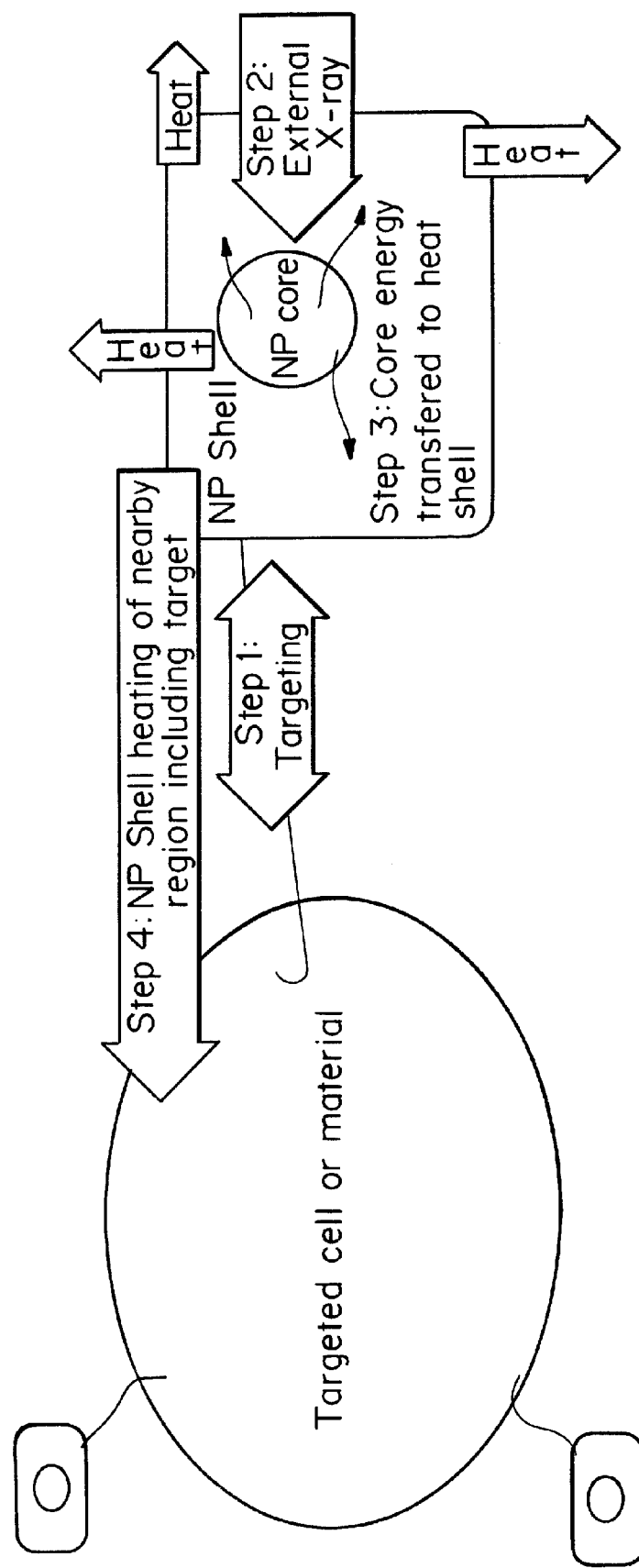
FIG. 1 is a schematic, not drawn to scale, of the method steps and physical entities. The first step involves positioning the nanoparticle into the region of the targeted material. The second step is exposing the targeted region to a source of external ionizing radiation, such as an x-ray, which the core material absorbs. The third step involves energy transfer from the nanoparticle core material to the nanoparticle shell for the purpose of heating the shell, through any of several mechanisms, one being overlap of the core emission spectrum with the shell absorption spectra (FRET). The fourth step is transfer of heat from the nanoparticle shell to the nearby region that includes the targeted material. Optionally, in the therapeutic embodiment, a fifth step may be removal of the nanoparticle from the patient through magnetic separation from the blood, whereby blood is taken from one arm of the patient, filtered, then returned through the other arm, in a procedure similar in clinical practice to conventional kidney dialysis.

The thermotherapy discussed here is for the imaging and treatment of diseases, including cancer. Hyperthermia is a long-established method of treating some diseases, but is most effective when it can be focused at the cellular or molecular level. Nanoparticles have been used to generate localized heat near a target cell, but existing methods have limitations in efficacy, cost and availability. Core-excited nanoparticle thermotherapy (CENT) represents a new paradigm in thermotherapy. The CENT method uses both core-excitation energy such as ionizing radiation (including x-rays) and core-shell nanoparticles, the nanoparticles being specifically designed to absorb the radiation in their core structure, then transfer energy from the core to the shell, so as to heat the shell of the nanoparticle. The heated nanoparticle then heats the surrounding region, to a temperature sufficient to detect, affect, damage or destroy the targeted cell or material. Such CENT nanoparticles can be bound to targeting agents that deliver them to the region of the diseased cell. The method also may include the removal of nanoparticles from the body. The method also enables the imaging of targeted cells or material.

I. Nanoparticles and Energy Sources for Use in Therapeutic Method

Nanoparticles have been developed which provide several advantages over previously described technology. First, in the preferred embodiment, this is a medical treatment method that exposes nanoparticles to x-rays for the purpose of producing therapeutic amounts of heat. Second, the nanoparticles have a core-shell configuration with a core that absorbs x-rays for the purpose of heating the shell. In other methods of cell-specific hyperthermia, such as near infrared ("NIR"), the nanoparticle core is inert and functions primarily to shift the maximum of the (plasmon resonance) absorption spectrum of the gold shell to higher wavelength, so as to overlap with an externally applied laser, at a frequency chosen in consideration of the "water window." Third, this method is unique with respect to the basic physics of how energy flows within the core-shell nanomaterial design. Specifically, an external source of energy is used to excite core material and then the excited core material then transfers energy to the shell to bring about plasmon excitation in the shell that heats the targeted cell. All other uses of nanomaterial for hyperthermia involve direct excitation of the plasmon resonance of the shell, usually gold, by external fields, whether electric, magnetic, radiofrequency ("RF") or NIR. Other forms of heating the core of the particles include other light, for example, applied with a laser or ultrasound. In those cases, energy flows, if at all, from the shell to the core. In other methods where nanoparticles are decorated with some amount of x-ray absorbing material, it is for the purpose of diagnostic detection, not for therapeutic heating. Fourth, the nanoparticles can be removed from the blood if desired. Fifth, this method can be coupled with other diagnostic tools, such as PET-CT scanners, to measure the efficacy of the method "in real time" and to determine the duration of the treatment session. Sixth, the method employs diagnostic and treatment equipment commonly found in hospitals, globally. Seventh, the technology combines therapy and diagnostics, in that x-ray (or gamma-ray) absorption is the basis for both diagnostic tools, such as CT scans, and for treatment. Finally, this method requires the coupling of the nanoparticle design to the irradiation regime for a given disease and patient.

As used herein, "nanoparticle" means one or more nanoparticles of any shape. As used herein, "nanoshell" means one or more "nanoshells" of any shape. As used herein, "shell" means one or more shells, of any shape. As used herein, "nanorod" means one or more nanorods, of any shape. The particles are generally referred to as "nanoparticles" unless otherwise specified. The nanoparticles consist of a shell and a core. As described below, the mechanisms by which heat is generated between these materials determines the composition and relative amounts of the shell and core materials. The main criteria for matching the core material to the shell material is that the radiation emission (wavelength distribution bell curve) from the core material should overlap the absorption spectrum (wavelength distribution bell curve) of the shell material. The nanoparticles typically have an average length or average diameter less than 1000 nm, preferably less than 500 nm, and most preferably less than 300 nm. The core material can be any diameter but is preferably less than 1000 nanometers, more preferably less than 500 nanometers. The thickness of the shell material is preferably less than 1000 nanometers, and most preferrably less than 200 nanometers. In the most preferred embodiment, the nanoparticles are less than 200 nanometers, which allows them to avoid being metabolized by the liver or kidneys.

The criteria for "activation or excitation energy" in the core is best described by the fundamental physical processes (atomic transitions) that cause the emission of the radiation. Core material may either generate intrinsic luminescence upon excitation by incident radiation or do so as a consequence of doping with ions, such as Europium, that serve the role of activators of luminescence. The incident radiation generates electron-hole pairs in the material. The relaxation of these electron-hole pairs results from a range of possible multistep mechanisms in the emission of photons in the ultraviolet, visible or near-infrared range of the spectrum. The mechanism of relaxation of ions excited by energy transfer from electron-hole pairs may involve either allowed or forbidden radiative transitions between quantized ionic or atomic energy levels. In the case of intrinsically luminescent core materials, the mechanism may involve the recombination of electron-hole pairs, radiative decay of free or trapped excitons, or core-valence transitions.

There are several potential mechanisms of energy flow within core-shell nanomaterials. One approach to facilitate transfer of x-ray energy within the core-shell structure is to induce core emission of radiation into the shell (FRET). There are several mechanisms of emissions from material that absorb x-rays, commonly referred to as scintillator materials. These mechanisms of scintillator emission of radiation include emissions from luminescent activator ions (e.g. $Ce^{3+}$, $Eu^{2+}$), from self-trapped excitons, from excitons bound to an isoelectronic hole trap (e.g. CdS:Te), from charge-transfer emissions (e.g. $CaWO_4$), and from core-valence transitions (e.g. $BaF_2$). In scintillator materials that do not contain a luminescent ion and where a specific emission mechanism is unknown, the event is considered to be self-activated. In short, emission is just one form of energy transfer by which energy in the core material can be transferred to (absorbed by) the shell.

Figure 2:
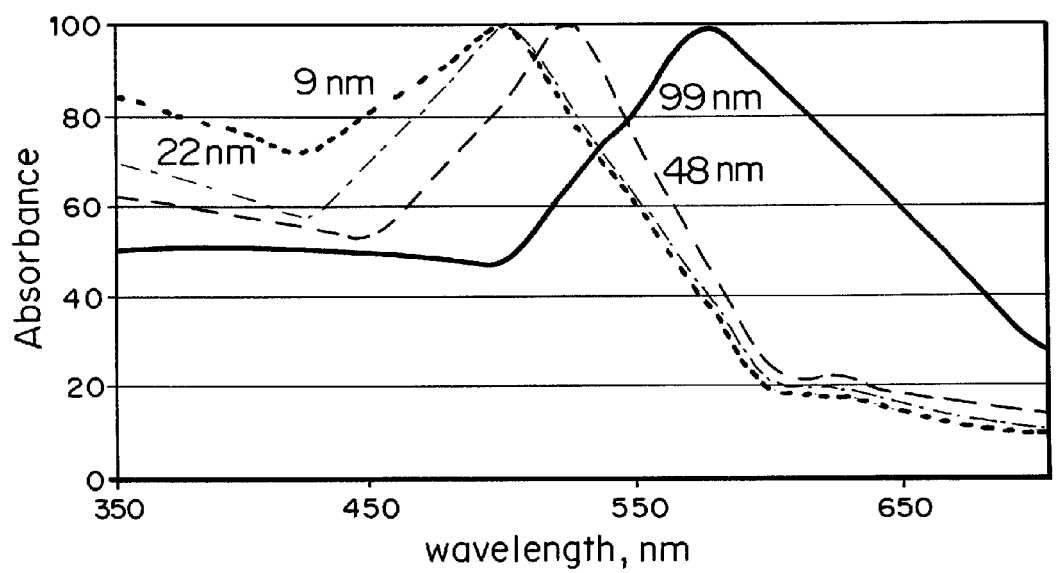
FIG. 2 shows the absorption spectra of gold nanoparticles of different diameters (from 9 to 99 nm), which ranges from 350 nm to 800 nm, with maximum absorbance for all diameters coming in the region of approximately 500 nm to 600 nm. (Taken from Link and El-Sayed, J. Phys. Chem. B, 103 (21):4212, 1999).
Figure 5:
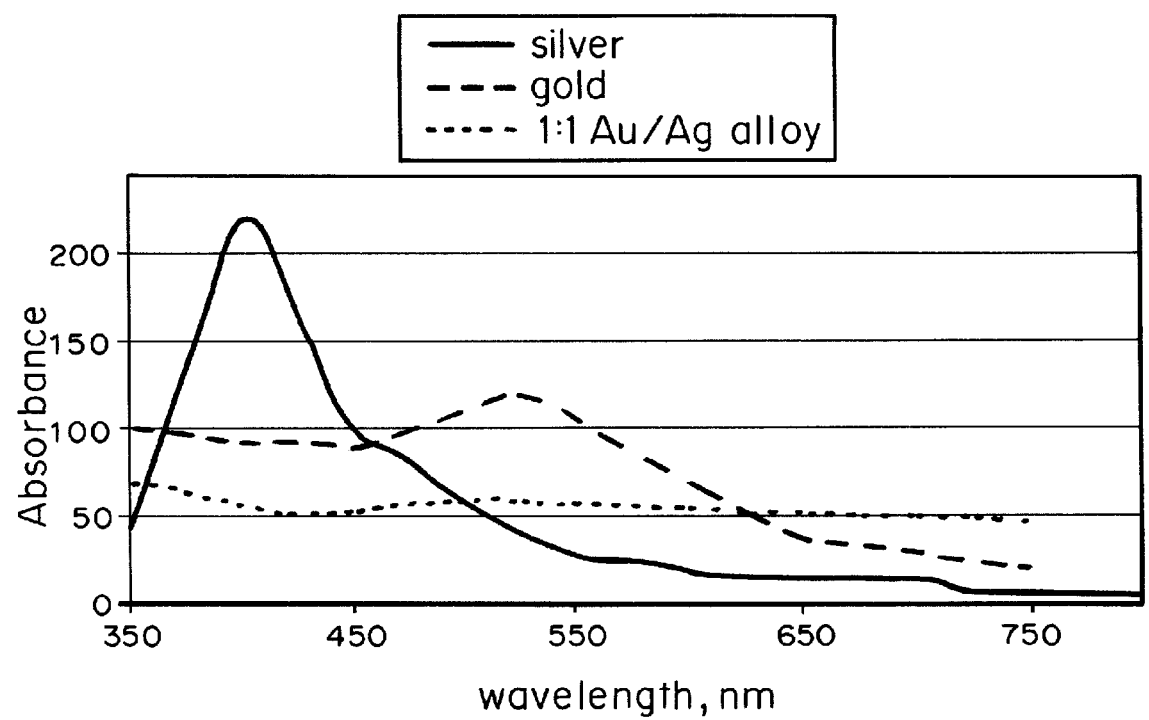
FIG. 5 shows the absorption spectra of gold and silver nanoparticles, which ranges from 350 nm to 800 nm. (Taken from Pal et al., *African Phys. Rev.* 1 (*Special Issue—Microfluidics*) (2007).
Figure 6:
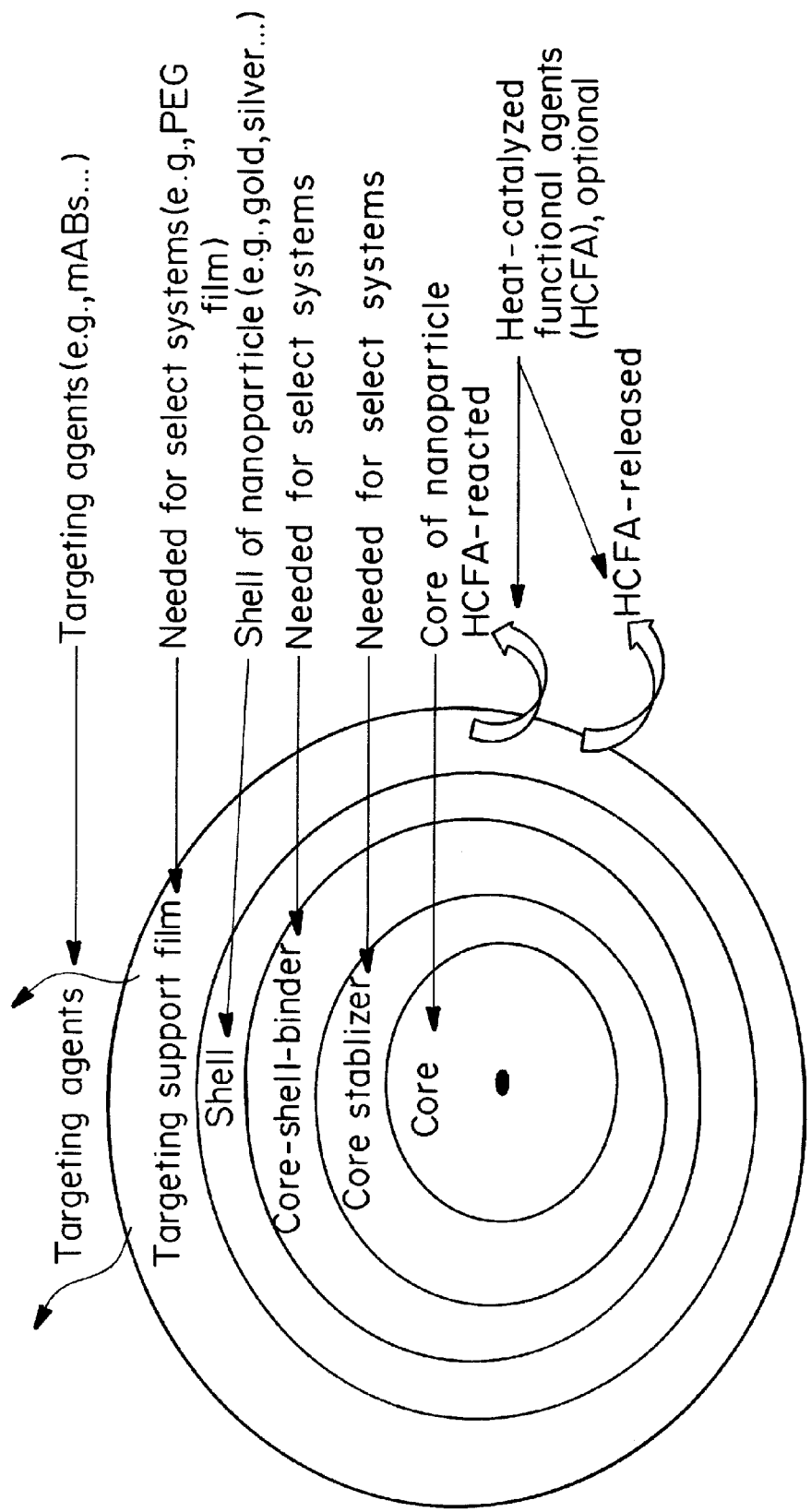
FIG. 6 is a schematic (not drawn to scale) of nanoparticle design. The nanoparticle core may need a film (or covering layer) to either ensure hydrolytic stability or allow binding to the shell inner layer (or two such films). Such layers are typically small, normally being less than 10 nm in thickness. The outer shell surface (e.g., gold) may need a supporting film (such as PEG) to allow one or more different types of targeting agents to be bound to the shell. Heat-catalyzed functional agents (such as chemotherapy compounds) may also be bound to the shell or targeting support film and released (or reacted) upon heating of the shell.

There are several considerations in the design of the nanoparticle shell. Along with safety, the shell must be i) transparent to x-ray or gamma-rays, ii) have a plasmon absorption spectrum that overlays the core emission (FRET), iii) be a good conductor of heat, and iv) allow attachment (if needed) of a targeting moiety and other species as needed. In the preferred embodiment, the shell comprises a significant amount of gold, silver, platinum, palladium or mixtures thereof. The plasmon absorbance spectrum of solid gold particles of about 10 nm in diameter have a maximum at around 520 nm, as indicated in FIG. 2. Silver has an absorption peak near 350-400 nm (FIG. 5). Zhou et al. ('94) have shown that modification in design of core material within a gold shell, such as adjusting the ratio of the core radius to the shell thickness (as well as the material composition of the core), can push the maximum absorbance of the gold shell into the range of 600 nm to 900 nm. In general, metal nanoshells have the unique property of having a tunable optical resonance (movable absorbance peak), which is critical to this invention, as it allows the flexibility needed to match core and shell energy flow channels to each other.

The shell and core structures must be designed as a single system. The geometric design of the core-shell structure guarantees that, when energy flow from core to shell is in the form of emitted radiation from the core, there is no energy loss due to emitted photons "missing" the shell. Almost 100% of the energy emitted is transmitted to the shell. However, if the x-ray absorbing material is placed on the shell, only a portion of the radiation emitted from this material would be emitted in the direction of the shell. Since the core-shell energy flow is within a particle, in the case of energy redistribution via intraparticle emission as discussed here (FRET), there is no need for fitting the excitation and absorbance into a "water window" (800-1300 nm and 1600-1850 nm) constraint that forces a preference for NIR over higher frequency (lower wavelength, higher energy) portions of the electromagnetic spectrum. For example, cores that emit in the visible or UV, and shells that absorb in the UV or visible, may be more preferred than NIR resonances for several reasons.

The nanoparticle core is made of one or more materials capable of undergoing scintillation luminescence, defined here as the reemission of electromagnetic radiation when excited by x-rays or gamma-rays. The nanoparticle core material absorbs energy then emits electromagnetic radiation as a result of a dopant ion, present at a minimum level to serve as an activator of luminescence. In preferred embodiments, the nanoparticle core contains a material doped with at least one rare-earth- or lanthanide-series (La, Ce, Pr, Nd, Pm, Sm, Eu, Gd, Tb, Dy, Ho, Er, Tm, Yb and Lu) element of the periodic table, in an amount greater than 0.1 mass percent. The nanoparticle core material can also be made of persistent luminescence nanoparticle materials, also known as long-lived phosphors or after-glow materials.

Examples of suitable core material include, but are not limited to, any form of strontium aluminate, such as $Sr_aAl_bO_c$, where a, b and c are integers that may vary (e.g., $Sr_4Al_{14}O_{25}$, $SrAl_2O_4$, $SrAl_2O_7$, and $Sr_3Al_2O_6$); any form of strontium aluminate doped with a rare earth element (RaE), $Sr_aAl_bO_c$:RaE, wherein a, b and c are integers that may vary and RaE=Ce, Pr, Nd, Sm, Eu, Tb, Dy, Ho, Er, Tm, or Yb in one or more oxidation states, such as Europium(II)-, Dysprosium(III)-, and Neodymium(III)-doped $Sr_4Al_{14}O_{25}$, $SrAl_2O_4$, $SrAl_2O_7$, and $Sr_3Al_2O_6$; any form of strontium aluminate co-doped with two or more different rare earth elements (RaEs), $Sr_aAl_bO_c$:$(RaE)_2$, wherein a, b and c are integers that may vary and RaE=Ce, Pr, Nd, Sm, Eu, Tb, Dy, Ho, Er, Tm, or Yb in one or more oxidation states, such as strontium aluminate co-doped with Europium(II) and Dysprosium(III) as in $Sr_4Al_{14}O_{25}$:$Eu^{2+}$:$Dy^{3+}$, $SrAl_2O_4$:$Eu^{2+}$:$Dy^{3+}$, $SrAl_2O_7$:$Eu^{2+}$:$Dy^{3+}$, and $Sr_3Al_2O_6$:$Eu^{2+}$:$Dy^{3+}$; and strontium aluminate co-doped with Europium(II) and Neodymium(III) as in $Sr_4Al_{14}O_{25}$:$Eu^{2+}$:$Nd^{3+}$, $SrAl_2O_4$:$Eu^{2+}$:$Nd^{3+}$, $SrAl_2O_7$:$Eu^{2+}$:$Nd^{3+}$, and $Sr_3Al_2O_6$:$Eu^{2+}$:$Nd^{3+}$; any form of rare-earth ion-doped gadolinium oxide or oxysulfide phosphor, $Gd_2O_3$:$RaE^{3+}$ or $Gd_2O_2S$:$RaE^{3+}$, wherein RaE=Ce, Pr, Nd, Sm, Eu, Tb, Dy, Ho, Er, Tm, or Yb; any rare-earth (RaE) ion co-doped alkaline earth aluminate, $xMO+yAl_2O_2$: RaE' RaE, where x and y are integers, and M=Ca, Sr, or Ba, and RaE=Ce, Pr, Nd, Sm, Eu, Tb, Dy, Ho, Er, Tm, or Yb; any rare-earth- or transition-metal-doped metal halide, including, but not limited to, $LaF_3$:$Ce^{3+}$, $LuF_3$:$Ce^{3+}$, $CaF_2$:$Mn^{2+}$, $CaF_2$:$Eu^{2+}$, $BaFBr$:$Eu^{2+}$, $BaFBr$:$Mn^{2+}$, $CaPO_4$:$Mn^{2+}$, $LuI_3$:Ce, $SrI_2$:Eu, $CaI_2$:Eu, $GdI_3$:Ce; or any other suitable material, such as CdS, CdSe, CdTe, $CaWO_4$, ZnS:Cu, TmO, ZnSe:Te, ZnS, ZnO, $TiO_2$, GaN, GaAs, GaP, InAs, InP, $Y_2O_3$, $WO_3$, and $ZrO_2$. These materials can be made by chemical synthesis, solid state reaction, other methods, or any combination thereof.

In some embodiments, the core is any form of strontium aluminate doped with Europium(II), such as $Sr_4Al_{14}O_{25}$: $Eu^{2+}$, $SrAl_2O_4:Eu^{2+}$, $SrAl_2O_7:Eu^{2+}$, or $Sr_3Al_2O_6:Eu^{2+}$. In some embodiments, the core is any of strontium aluminate co-doped co-doped with Europium(II) and Dysprosium(III), such as $Sr_4Al_{14}O_{25}:Eu^{2+}:Dy^{3+}$, $SrAl_2O_4:Eu^{2+}:Dy^{3+}$, $SrAl_2O_7:Eu^{2+}:Dy^{3+}$, or $Sr_3Al_2O_6:Eu^{2+}:Dy^{3+}$. In some embodiments, the core material is a semiconductor nanomaterial such as ZnS, ZnO, or $TiO_2$. In preferred embodiments, the core is any form of strontium aluminate $Sr_wAl_xO_y$ doped with $Eu^{2+}$, $Dy^{3+}$, $Nd^{3+}$, or combinations thereof, wherein the ratio of "y/x" is from 1 to 10 and/or the ratio "w/x" is from 1 to 10 (e.g., $Sr_4Al_{14}O_{25}$, $SrAl_2O_4$, $SrAl_2O_7$, and $Sr_3Al_2O_6$ doped with $Eu^{2+}$, $Dy^{3+}$, $Nd^{3+}$, or combinations thereof).

In addition to the core and shell, the nanoparticle can optionally contain one or more additional layers. In some embodiments, the nanoparticle core is surrounded by or has integrated into a core stabilizer (i.e. a film or covering layer to ensure the hydrolytic stability of the core). In some embodiments, the nanoparticle contains a core-shell binder (i.e. a film or layer between the nanoparticle core and shell facilitate binding of the core to the inner layer of the nanoparticle shell). Non-limiting examples of such films include phosphates and amines. In some embodiments, the shell of the nanoparticle is coated with a targeting support film (e.g., polyethylene glycol) which serves as a point of attachment for targeting ligands and/or HCFAs. Additional particle layers are typically small, normally less than 10 nm in thickness, and are introduced into the particle without causing significant detriment to energy flow between the core and shell.

B. Energy Sources

The term "energy source" refers to any form of excitation, including high-energy particles and radiation from all regions of the electromagnetic spectrum; ultrasound, electric fields and magnetic fields. Such sources can be used in exciting atoms, molecules, chemical complexes, composite particles or nanomaterials. The term "exposure" herein means an irradiation regime, for either diagnostic or therapeutic purposes, that may include i) single events or multiple events, ii) in one session or many sessions over many years, or iii) involve a single particle or photon or a wide spectral range of photons.

A suitable x-ray is any electromagnetic radiation that is sufficient to pierce the human body; preferable x-rays are those with wavelengths less than 10 nanometers, more preferably those with wavelengths between 10 and 0.001 nanometers. The power and pulsing of the x-ray must be sufficient to bring about the desired heating of the target cell, which may vary among diseases and patients. X-ray devices that may be used in the methods herein include conventional commercial x-ray units commonly used for diagnostic or therapeutic purposes, computed-tomography (CT) scanners, full-body scanners or even x-ray lasers.

X-rays are advantageous because of both their ability to penetrate through the entire body and the amount of energy contained within the x-ray photon. But other high-energy sources, such as gamma rays, and high-energy particles can also be used. The critical feature in the source of the external energy is whether one can design the core material of the nanoparticle to both absorb the energy and then direct the energy flow into exciting a plasmon resonance of the outer shell so as to generate heat.

A suitable range of gamma-ray radiation is an amount sufficient to pierce the human body and excite the nanoparticle core material, to begin step 2 of the process, as outlined in FIG. 1. Electromagnetic radiation in the wavelength range of 0.01 to 0.00001 nm is typically considered gamma radiation.

High-energy particles include positrons, such as those used in positron emission tomography (PET) scans, and high-energy protons and electrons and are useful as external sources of energy.

The term "electromagnetic radiation" includes radiation having propagating perpendicular electric and magnetic fields, and is limited to the range of microwaves through cosmic rays.

Ionizing radiation consists of particles or electromagnetic waves that are energetic enough to detach electrons from atoms or molecules, thereby ionizing them. Direct ionization from the effects of single particles or single photons produces free radicals, which are atoms or molecules containing unpaired electrons, that tend to be especially chemically reactive due to their electronic structure. The degree and nature of such ionization depends on the energy of the individual particles (including photons), not on their number (intensity). In the absence of heating or multiple absorption of photons, an intense flood of particles or particle-waves will not cause ionization if each particle or particle-wave does not carry enough individual energy to be ionizing (e.g., a high-powered radio beam). Conversely, even very low-intensity radiation will ionize, if the individual particles carry enough energy (e.g., a low-powered X-ray beam). Roughly speaking, particles or photons with energies above a few electron volts (eV) are ionizing, no matter what their intensity. Examples of ionizing particles are alpha particles, beta particles, neutrons, and cosmic rays. The ability of an electromagnetic wave (photons) to ionize an atom or molecule depends on its frequency, which determines the energy of its associated particle, the photon. Radiation from the short-wavelength end of the electromagnetic spectrum, high-frequency ultraviolet, X-rays, and gamma rays, is ionizing, due to their composition of high-energy photons. Lower-energy radiation, such as visible light, infrared, microwaves, and radio waves, are not ionizing.

A scintillator is a material which exhibits the property of luminescence when excited by ionizing radiation. Luminescent materials, when struck by an incoming particle, absorb its energy and scintillate, i.e. reemit the absorbed energy in the form of a small flash of light, typically in the visible range. If the reemission occurs promptly, i.e. within the approximately $10^{-8}$s required for an atomic transition, the process is called fluorescence. Sometimes, the excited state is metastable, so the relaxation back out of the excited state is delayed, necessitating anywhere from a few microseconds to hours depending on the material. The process then corresponds to either one of two phenomena, depending on the type of transition and hence the wavelength of the emitted optical photon: delayed fluorescence or phosphorescence (also called after-glow). Since it is critical to supply a source of continuous heating of the targeted material to induce hyperthermia, these two phenomena, delayed fluorescence and phosphorescence, represent two ways of heating the nanoparticle shell from the inside. A third approach is to use a sequence of high luminosity x-ray scintillations.

There are two basic approaches to the design of the core-shell nanoparticle system if FRET is the method of intraparticle energy flow from the core to the shell. The first approach is to use high luminosity materials that emit large amounts of energy, but only for a short time after the excitation pulse (here the x-ray) is terminated. Repeated pulses of x-ray excitation are required for shell heating. The second approach is to use materials that emit for much longer periods of time but at a lower intensity. More than one excitation dose of (x-ray) radiation may be necessary and applied. Within the core material, the energy depth of electron traps, and the number of electron traps, in the nanomaterial are the main factors in designing a nanomaterial with long and intense afterglow performance. (Chang et al *J. of Alloys and Compounds*, 415: 220-224, 2006).

Existing research (Kirui et al, 2010) suggests that, for some diseases, a less rapid elevation in temperature, along with a less elevated temperature level that is sustained over longer time periods, offers more selective destruction of targeted cells, than does rapid high-powered heating. Therefore, the CENT treatment paradigm includes nanoparticle designs and irradiation schemes that cover the extremes of treatment approaches, from rapid heating and destruction of targeted species (seconds) to much longer periods (days) of continuous therapeutic heating by CENT nanoparticles.

In the first approach above, the nanoparticle core is made from high luminosity scintillation material, which is then subjected to a series of x-ray pulses over time to heat the nanoshell. X-ray excited scintillation luminescence is the common term given to this excitation. Moses et al., IEEE Trans. Nucl Sci., NS-45, 462, 1998, discuss dense infrared emitting scintillators. The infrared (and NIR) radiation band is just one portion of the electromagnetic spectrum that can be used, but is useful as an example because of the data summarized in Table 1. More specifically, in Tables 1 and 2 of the Moses et al. publication, the authors note that rare earth elements and other specific ions, when used as dopants into the proper host material, can have intense room temperature luminescent emissions in the 200-1100 nm range. The website http://scintillator.lbl.gov lists critical scintillator properties, from which Table 2 below was constructed. The first entry in Table 2 is of $LuI_3$, doped with Ce. The mechanism of scintillation is based on the $Ce^{3+}$ ion. This material has high luminosity in that 98,000 photons at 540 nm (visible) are emitted for every MeV of x-ray energy that is absorbed; but the emission is relatively long for scintillation (a duration of 10 microseconds). The binding of this material within a gold or silver shell is guided by the reported synthesis of a hybrid nanoparticle of AgI and gold (Au), (J. Phys. Chem. 104, 4031, 2000), offering evidence of metal iodides binding with gold.

TABLE 2

X-ray Excitation of High Luminosity Scintillation Materials

| Formula | Mechanism | Photons/MeV Luminosity | Emission duration (nanoseconds, ns) | Emission Peak (nanometers) |
|---|---|---|---|---|
| $LuI_3$:Ce | Ce3+ | 98,000 | 10 microseconds | 540 nm |
| $SrI_2$:Eu | Eu2+ | 120,000 | 1200 ns | 435 nm |
| $CaI_2$:Eu | Eu2+ | 86,000 | 790 ns | 470 nm |
| $GdI_3$:Ce | Ce3+ | 89,000 | 33 ns | 563 nm |

U.S. Pat. No. 4,499,005 to McColl et al. discloses the use of thulium (Tm), along with silver coactivated zinc sulfide in an infrared-emitting phosphor that emits at 800 nm. This finding is in agreement with that reported in Moses et al., where the $Tm^{+3}$ ion transitions of $^3H_4 \rightarrow {}^3H_6$ and $^1G_4 \rightarrow {}^3H_5$ correspond to 800 nm when the $Tm^{+3}$ powders of $YPO_4$:2%Tm and $LuPO_4$:2%Tm, were excited with x-rays in the 20-30 KeV range. The $YPO_4$:2%Tm material was reported to yield 9242 photons/MeV (this value may be high due to the nature of the powdered sample). Importantly, rare-earth-based materials can be used to form nanorods, as demonstrated by Das et al., Langmuir, 26(11):8959 (2010), and references therein. As shown in FIG. 5 of the Das et al. publication, significant luminescence in the 500-700 nm range occurs upon excitation of nanorods of Yb/Er-co-doped $Gd_2O_3$.

Figure 4A:
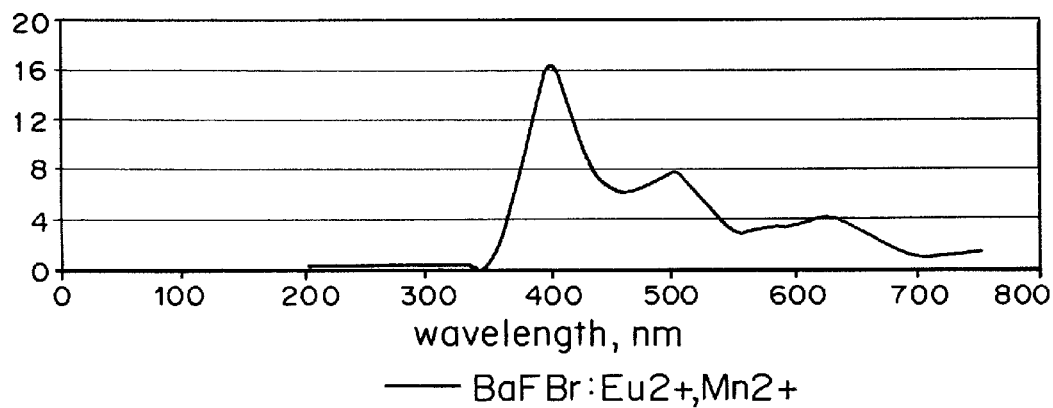
FIGS. 4a and 4b show the x-ray luminescence spectrum of two nano-scintillator materials. X-axis is in nm, while the y-axis is intensity in arbitrary units.
Figure 4B:
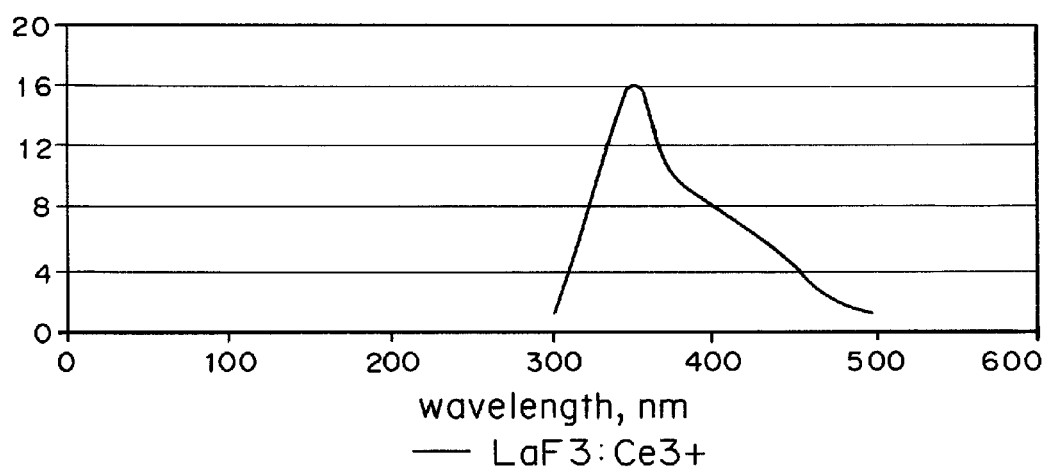

In the above second approach to designing the desired CENT nanoparticles, the nanoparticle core is made from long-lived luminescence material, employing x-ray (or gamma ray) excited persistent luminescence, the basic mechanisms of which are either delayed fluorescence or phosphorescence (also known as long-lived phosphors or after glow). Select members of these classes of materials absorb high energy x-rays and then emit radiation in a spectral range that overlaps the absorption spectrum of important metal nanoshells, including gold. As an example, FIG. 4(a) shows the x-ray luminescence spectrum of BaFBr:Eu2+, Mn2+ nanoparticles, while FIG. 4(b) shows the similar spectrum of LaF3:Ce3+. These emission spectra (from Chen and Zhang, 2006) match well the absorption spectra of gold nanoshells (FIG. 2). These authors, who designed the materials with a well-designed "trap system" to sustain luminescence, report that emitted light from their nanoparticles exceeds an intensity of 25 mW/cm². Strontium aluminate ($SrAl_2O_4$) has been recognized for decades as a long-lived phosphor. Europium ($Eu^{2+}$) doped versions of $SrAl_2O_4$ are also well known as a further enhancement. More recent enhancements include co-doping with $Eu^{2+}$ and $Dy^{3+}$ for long "afterglow" duration, which have been well studied and are available commercially as noted in the commercial products listed in Table 3 below.

TABLE 3

Select Commercial Long-lived (afterglow) Phosphors

| Supplier | Product composition | Emission time | Emission peak, nm |
|---|---|---|---|
| MolTECH Gmbh | SrAlO4:Eu,Dy | 15-18 hours | 530 nm |
| MolTech Gmbh | CaAlO4:EuDy | 8-10 hours | 440 nm |
| Boston ATI | $SrAl_2O_4$:Eu | 10 hours | 525 nm |
| Boston ATI | $Sr_4Al_{14}O_{25}$:Eu | 10 hours | 490 nm |

Therefore, persistent luminescence from a nanoparticle core can supply the total energy needed to supply a lethal level of heat to tumor cells. In comparison to the total energy deposited into the gold nanoshells proven effective for NIR ablation of human colorectal tumors in mice, as suggested by the entries in Table 1, a core emission of 25 mW/cm² for a period of 7 hours is necessary. The implicit assumption in this calculation is that the skin of the nude mice is transparent to the 800 nm NIR, just as one assumes that the transfer from the CENT core to the shell is 100% efficient.

Photodynamic therapy (PDT) is a therapeutic approach to disease, including cancer, whereby singlet oxygen is generated in vivo (or in vitro) by light. Singlet oxygen then plays a central role in the attack on the cancer cell. Scintillation and persistent luminescent materials are two classes of materials of research interest in PDT, that have x-ray excited emission in the 350 nm to 750 nm range with long lifetimes. Researchers in PDT have worked with long-lived luminescence, but their application is not related to thermotherapy, nor do they consider coating their nanoparticles with a metal shell. As expected by their need for visible light, the nanomaterials discussed in PDT research literature employ an emission spectrum that could be made to overlap the absorption spectrum needed to heat gold (or silver) nanoshells. Also importantly, these scintillation and persistent luminescent materials have been shown to be useful for fabrication into nanoparticles for use in the generation of singlet oxygen for PDT. (Chen and Zhang, 2006).

C. Targeting Molecules

Systemically administered nanoparticles may be targeted so that they travel to a desired location where they are retained until activated by an energy source. They may also be sized so that they are administered to an area and then retained as the nanoparticles are trapped within smaller blood or lymph vessels into the tissue. A targeting molecule is a substance which will direct the particle to a receptor site on a selected cell or tissue type, can serve as an attachment molecule, or serve to couple or attach another molecule. As used herein, "direct" refers to causing a molecule to preferentially attach to a selected cell or tissue type. This can be used to direct cellular materials, molecules, or drugs, as discussed below.

Targeting ligands include any molecule that recognizes and binds to target antigen or receptors over-expressed or selectively expressed by particular cells or tissue components. These may include antibodies or their fragments, peptides, glycoproteins, carbohydrates or synthetic polymers. Specificity is determined through the selection of the targeting molecules. The effect can also be modulated through the density and means of attachment, whether covalent or ionic, direct or via the means of linkers. Targeted particles which have therapeutic compounds such as drugs, cellular materials or components, and antigens, and have targeting ligands directly bound to the particle surface can be used to induce cellular immunologic responses or as therapeutics. Targeting greatly increases specificity, while not decreasing therapeutic load, such as DNA vaccines, drugs, peptides proteins or antigens. Another advantage is that more than one material can be encapsulated and/or coupled to the surface of the particle. This may be a therapeutic and/or targeting material.

Targeting molecules can be proteins, peptides, nucleic acid molecules, saccharides or polysaccharides that bind to a receptor or other molecule on the surface of a targeted cell. The degree of specificity can be modulated through the selection of the targeting molecule. For example, antibodies are very specific. These can be polyclonal, monoclonal, fragments, recombinant, or single chain, many of which are commercially available or readily obtained using standard techniques. Antibodies, peptides and aptamers are just a few ways of identifying and selectively binding to both nanoparticles and tumor cells. For example, the cell-surface differentiation antigen A33 is a glycoprotein that is expressed in greater than 95% of primary and metastatic colon cancer cells, but absent in normal cells. (US 2009/0263394 A1 by Scanlan et al.) Antibodies developed against the A33 antigen bind to tumor cells and exhibit prolonged retention in tumor tissue. A mouse monoclonal antibody (mAb), and a humanized version (huA33), have been developed and radio-labeled for studies. These antibodies can be attached to a gold metal surface through use of a polyethylene glycol (PEG) derivative. An excellent review of targeting molecules and nanoparticles to tumors is by Ruoslahti, Nat. Rev. Cancer, 2:83-90, 2002. For breast cancer, the recombinant humanized monoclonal antibody trastuzumab (mAb-trz) has seen most use as an imaging agent, when labeled with the radioisotope zirconium Zr 89, with radioisotopic activity. The trastuzumab moiety of zirconium Zr 89 trastuzumab binds with high affinity to the extracellular domain of human epidermal growth factor receptor 2 (HER2). Upon binding, the radioisotope moiety can be used in positron emission tomography (PET), allowing the imaging and quantification of HER2-expressing tumor cells. HER2, a tyrosine kinase client protein of heat shock protein 90 (Hsp90), may be over expressed on the cell surfaces of various tumor cell types; most current research on mAb-trz involves breast cancer.

Examples of molecules targeting extracellular matrix ("ECM") include glycosaminoglycan ("GAG") and collagen. Molecules which target Toll-like Receptors (TLRs) on the surface of the cells or tissue, or signal the cells or tissue internally, may increase uptake. Pathogen-associated molecular patterns (PAMPs) conjugated to the particle surface or co-encapsulated may include: unmethylated CpG DNA (bacterial), double-stranded RNA (viral), lipopolysaccharide (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic). In another embodiment, the outer surface of the particle may be treated using a mannose amine. This treatment may cause the particle to bind to the target cell or tissue at a mannose receptor on the antigen presenting cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue. Lectins that can be covalently attached to render them target specific to the mucin and mucosal cell layer include lectins isolated from *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique,* as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius,* and *Lotus tetragonolobus.* The attachment of any positively charged ligand, such as polyethyleneimine or polylysine, to any particle may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Polyclonal antibodies raised against components of mucin or else intact mucin, when covalently coupled to particles, provide for increased bioadhesion. Similarly, antibodies directed against specific cell surface receptors exposed on the lumenal surface of the intestinal tract would increase the residence time of beads, when coupled to particles using the appropriate chemistry. The ligand affinity need not be based only on electrostatic charge, but other useful physical parameters such as solubility in mucin or else specific affinity to carbohydrate groups. The covalent attachment of any of the natural components of mucin in either pure or partially purified form to the particles would decrease the surface tension of the bead-gut interface and increase the solubility of the bead in the mucin layer. Useful ligands include: sialic acid, neuraminic acid, n-acetylneuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface. The attachment of polyamino acids containing extra pendant carboxylic acid side groups, e.g., polyaspartic acid and polyglutamic acid, also provide a useful means of increasing bioadhesiveness. Using polyamino acids in the 15,000 to 50,000 kDa molecular weight range would yield chains of 120 to 425 amino acid residues attached to the surface of the particles. The polyamino chains would increase bioadhesion by means of chain entanglement in mucin strands as well as by increased carboxylic groups.

Methods are known for attachment of the targeting ligands to the nanoparticles. For example, WO 2007/02493 to Semprus describes grafting sulfobetaine and carboxybetaine from self-assembled monolayers on gold substrates or from silyl groups on glass substrates using atom transfer radical polymerization (ATRP). For metallic and ceramic substrates, increased surface area can be created through surface roughening, for example by a random process such as plasma etching. Alternatively, the surface can be modified by controlled nano-patterning using photolithography. For the development of surface-functionalized gold nanoparticles as cellular probes and delivery agents, hetero-bifunctional poly (ethylene glycol) (PEG, MW 1500) having a thiol group on one terminus and a reactive functional group on the other can be synthesized for use as a flexible spacer. Using the PEG spacer, the gold nano-platform can be conjugated with a variety of biologically relevant ligands. See also El-Sayed, et al., Nanoletters, 5(5):829-834 (2005) describing methods for conjugating antibodies to gold nanoparticles.

D. Heat-Catalyzed Functional Agents

The nanoparticles can also be functionalized with, or administered with, one or more heat-catalyzed functional agents (HCFAs). HCFAs can be any therapeutic, prophylactic, or diagnostic agent which is bound to or associated with the shell or targeting support film of the nanoparticle, and is released (or reacted) when the particle is activated by an energy source. For example, HCFAs can be bound to the nanoparticle shell or targeting support film by a chemical bond which is cleaved as the nanoparticle is heated, releasing the HCFA. Alternatively, the HCFAs can be encapsulated in a thermally sensitive liposome or polymer microcapsule, and released upon initiation of thermotherapy at the specific site where the nanoparticles have been targeted or delivered. In some embodiments, the HCFA is an anti-neoplastic agent. In such cases, the anti-neoplastic agent is released or reacted when and where the particle is activated by an energy source. Accordingly, the anti-neoplastic agent can be selectively administered in the vicinity of cancer cells. Administration of the anti-neoplastic agent locally and in combination with thermotherapy lowers the effective dose of anti-neoplastic agent required to treat cancer. In some embodiments, multiple HCFAs are bound to the nanoparticle and administered concomitantly.

Examples of suitable anti-neoplastic agents include, but are not limited to alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as irinotecan and topotecan and derivatives of epipodophyllotoxins such as amsacrine, etoposide, etoposide phosphate, and teniposide).

Cancer immunotherapy can be effective in the treatment of select cancer patients with disease poorly amenable to conventional therapy. In preferred embodiments, the HCFA is an immunomodulator. In some embodiments, the HCFA is monoclonal antibody, for example, an epidermal growth factor receptor (EGFR) inhibitor (for example, Erbitux) or an angiogenesis inhibitor (for example, Bevacizumab). In further embodiments, the HCFA is a cytokine. Cytokines are cell-signaling proteins that are important in enhancing both innate (e.g., inflammation, macrophages) and adaptive (B- and T-cell) immune responses. Cytokines can be therapeutically administered to strengthen immune response and overcome tumor suppressive mechanisms. However, there are significant limitations to administering cytokines via traditional methods, foremost being their toxicity and poor drug half-life in circulation. Cytokines (including interferon-alpha (INF-$\alpha$), interferon-beta (INF-$\beta$), interferon-gamma (INF-$\gamma$), interleukin-2 (IL-2), interleukin-12 (IL-12), and granulocyte-macrophage colony-stimulating factor (GM-CSF) can be incorporated as HCFAs and released locally when and where the particle is activated by an energy source. Accordingly, the toxicity associated with the systemic administration of cytokines can be mitigated.

II. Method of Treatment

A. Diseases and Disorders to be Treated

The nanoparticles can be administered to an individual to kill endogenous tissue or cells. The tissue can be undesirable tissue that has arisen due to transformation, such as a tumor, cancer, or endometriosis; adipose tissue; plaques present in vascular tissue and over-proliferation such as those formed in restenosis; birthmarks and other vascular lesions of the skin; scars and adhesions; and irregularities in connective tissue or bone, such as bone spurs. As used herein, the term "cancer" includes a wide variety of malignant solid neoplasms. These may be caused by viral infection, naturally occurring transformation, or exposure to environmental agents. Parasitic infections and infections with organisms, especially fungal, that lead to disease may also be targeted.

The nanoparticles are used to diagnose or treat diseases by inducing hyperthermia in or near targeted entities. Targeted entities may include organs, cells, clusters of cells, molecules within cells or other molecular species. The diseases of interest include those where an increase in temperature of the target species brings about a desired result, and where a modest amount of localized heat may catalyze beneficial reactions, whereas a large amount of heat may be intentionally destructive. For example, heat that is sufficient and selective enough to bring about death of a targeted a cancer cell, and result in overall improvement of the patient, is preferred.

B. Therapy

The therapeutic method is summarized in a series of steps, as outlined in FIG. 1. The first step in the method involves delivering the nanoparticles into the region of the targeted material or cell. This can be achieved by physically injecting the nanoparticles into tissue or by employing chemical forces among molecules, such as antigen to antibody complexing using monoclonal antibodies to link the nanoparticle to sites on the cell surface. The second step in the method is the application of external ionizing radiation (primarily x-rays) for the purpose of exciting the core of the nanoparticle. The third step in the method is the transfer of energy from the nanoparticle core to the nanoparticle shell. One method of such energy transfer is frequency resonance energy transfer (FRET), which is achieved when the emission spectrum of the core material overlaps the absorption spectrum of the shell material, allowing plasmon excitation in the nanoshell that heats the nanoshell. The fourth step of the method is heat transfer from the nanoshell to the surrounding fluid region, which includes the targeted material or cell, to bring about the desired change, damage or cell death.

For a given treatment session or diagnostic test, the irradiation regime to which the nanoparticles are exposed is dependent upon several factors. The compositions and design of the nanoparticle core and shell determine the amount of heat that can be emitted from the nanoparticle. Another consideration is the ability of the targeting method to deliver nanoparticles into the desired region of the cell or tissue. Another consideration is whether the objective of the procedure is diagnostic or therapeutic. Another consideration, in the case of a therapeutic method, is the maximum safe dose of radiation that can be tolerated by the patient. Another consideration, which depends upon the targeted cell or material, is the amount of heat required to bring about the desired effect.

The nanoparticles can be administered systemically or locally, by injection into the bloodstream, the tissue to be killed, or other lumens or cavities or vessels into the tissue or region of cells to be killed. The nanoparticles may be administered by direct injection through a syringe or catheter, before the x-ray radiation is applied. In other scenarios, the nanoparticles are intravenously administered, thereby employing targeting schemes that depend on chemical interaction; then, either specific organs, parts of organs, or regions of the body are treated with the necessary dose of x-ray radiation.

The nanoparticle core or shell material, or portion thereof, may be removed from the body. In such cases, the nanoparticle may be decorated or doped with magnetic material, typically on the shell surface, to allow magnetic removal of the particle from the blood by established cell-separation techniques.

As used herein the term "dose" represents a concentration of absorbed energy, such as electron volt (eV) per gram (gm) or Grey (Gy). The quantity termed "dose length product," DLP, represents total energy imparted to the body and is the product of the dose and the volume of tissue exposed.

Research over the last decade involving in vivo heating of human cancers using gold nanoparticles, allows one skilled in the art to estimate the necessary energy input into gold nanoshell plasmon modes, to destroy significantly sized tumors of human cancers or other tissues. Tumors in nude mice can be killed when lasers in the 808-820 nm (NIR) wavelength range are used to irradiate skin covering a tumor of volume of less than 1 cubic centimeter (cm), for durations ranging from 2 to 5 minutes, with surface power densities ranging from 2 to 4 Watts/cm². These literature studies are summarized in Table 1.

TABLE 1

Select Studies of NIR Heating of
Gold Nanoparticles in Tumors in Mice

| Cancer Type | Type of Particle | NIR ($\lambda$, nm) | Exposure time, energy | Lit. Reference |
|---|---|---|---|---|
| Mice | mda-mb-435 nanorods | 810 nm | 5 min, 2 W/cm² | von Maltzahn 09 |
| Mice | ct26.wt peg-ns 130 nm | 808 nm | 3 min, 4 W/cm² | O'neal et al. '04 |
| Mice | canine tvt tuned-ns | 820 nm | <6 min, 4 W/cm2, 5 mm | Hirsch et al '03 |

Nanoparticles embedded throughout the tumor volume are responsible for the conversion of NIR into heat which causes cell death, as either NIR exposure or nanoparticle presence alone are shown to not be cytotoxic. In these studies, total laser energy deposited into the tumor is on the order of 2000 MeV. Additionally, tumors of this size are composed of, at least, billions of cancerous cells. Therefore, on a per cancer cell basis, rough estimates of 1 eV delivered into the gold shell plasmon resonance is sufficient to generate the heat necessary to bring about cancer cell death in these studies.

As a reference point for the therapeutic dosages of x-ray radiation needed, a patient of 180 cm in height and 80 Kg in weight, undergoing a state-of-the-art commercial CT scan of the chest, abdomen and pelvis (a body region approximately representing half his weight and height) may typically receive x-ray pulses with a range of energies usually 20 to 120 KeV, with an 80 KeV peak, with a total CT radiation dose (dose length product, DLP) of 1300 mGy-cm. The entire scan may represent 200 to 300 individual x-rays, separate "slices" through the examined region at a spacing of approximately two images per cm (typically about 1010 photons per cm²). State-of-the-art CT scanners submit the patient to a "cork screw" of continuous radiation, as the x-ray source rotates around the patient, from which the "slices" or images are computed. Therefore, the exposed region of the body (40 Kg and 90 cm) has received a dose of approximately $10^8$ MeV/gm. If the patient has a tumor volume of 1 cm³, of approximate density of about 1 g/cm³, that volume has received approximately $10^8$ MeV/gm of x-ray radiation. The biological response to the radiation is not considered in the DLP calculation.

In comparison to the approximate 2000 MeV of laser energy deposited into the gold plasmons, which was converted into heat to destroy nearby tumors, in the mice studies of Table 1, conventional x-ray treatments supply an ample source of energy within the body to bring about the death of cancer cells, if the energy is converted to thermal energy and targeted properly. The nanoparticles described herein are characterized by the efficient conversion of ionizing (primarily x-ray) radiation into focused thermal energy.

Most of the elements used in the particles are safe to administer and leave in patients. However, nanoparticles may be removed from the blood by magnetic separation techniques. Colloidal gold particles (aurothiomalate, auranofin) have been used in the treatment of patients with rheumatoid arthritis (Jessop et al., *Br J Rheumatol* 37:992-1002, 1998; Bassett et al., *Liver Int* 23:89-9,. 2003). Nanoparticle-based contrast agents for MRI, CT and PET imaging have drawn much interest. The rare-earth element gadolinium (metal chelate ion $Gd^{3+}$) is used in one such contrast agent, indicating the relative utility and safety of this material.

The present invention will be further understood by reference to the following non-limiting hypothetical examples.

EXAMPLES

Example 1

Targeting Breast Cancer

The following CENT treatment approach is based on a core-shell nanoparticle designed on the basis of X-ray excited persistent luminescence and the maximum safe dose of x-ray radiation the patient may tolerate. As a reference point for the therapeutic dosages of x-ray radiation needed, the patient is 180 cm in height and 80 Kg in weight.

Figure 3:
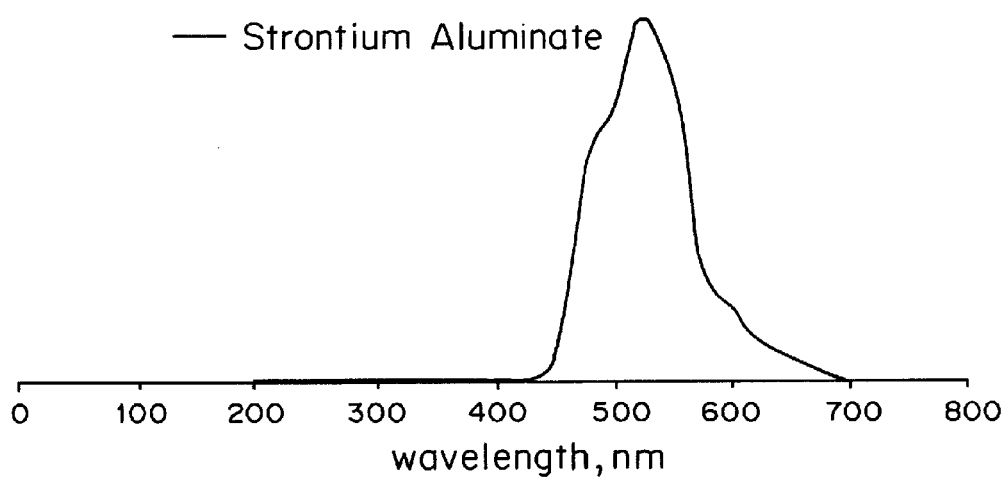
FIG. 3 shows the X-ray emission spectrum of Europium-activated strontium aluminate, with a material formulation of 0.9 parts Strontium (Sr) and 1 part $Al_2O_3$ and 0.03 parts EuO. Taken from U.S. Pat. No. 3,294,699 to Lange.

First, nanoparticles of $SrAl_2O_4$:Eu:Dy of approximately 60 nm in diameter, prepared by solid state reaction methods, are used as the core in a core-shell nanoparticle material design. The x-ray luminescence spectrum of this material has a maximum at approximately 510 nm, similar to the non-doped SrAl₂O₄ material, as shown in FIG. 3. A nanoshell of gold is grown over the nanocore material. Gold nanoparticles have the absorbance spectrum typical of that shown in FIGS. 2 and 5; additional Mie theory calculations allow design for maximum spectral overlap (FRET) between core and shell. The nanoparticle is then coated with polyethylene glycol (PEG), to which the trastuzumab antibody is attached. The nanomaterial is further processed for preparation of intravenous administration into a patient with early stage breast cancer.

After administration of the nanoparticles, sufficient to allow targeting to the diseased cells, the patient is prepared for a CT (x-ray) irradiation regime. The therapeutic portion of the CT irradiation scheme is optimized based on several factors, including 1) the nanoparticle being used, 2) the organ or body region being treated (here, the breast), 3) the disease being treated (here breast cancer), 4) the goal of the treatment and 5) the size of the patient (patient safety). If several exposures of x-ray radiation are to be necessary to generate the required therapeutic heating, the maximum safe dose to the patient determines the appropriate regimen.

Example 2

Treatment of Colon Cancer

The following CENT treatment approach is based on a core-shell nanoparticle designed on the basis of X-ray excited persistent luminescence and the maximum safe dose of computed tomography (CT) radiation the patient may tolerate. As a reference point for the therapeutic dosages of x-ray radiation needed, the patient is 180 cm in height and 80 Kg in weight.

First, nanoparticles of BaFBr:Eu²⁺,Mn²⁺ of 20 nm in diameter are prepared as the core material as outlined in Chen and Zhang, 2006. The x-ray luminescence spectrum of this material has a maximum at approximately 400 nm, as shown in FIG. 4(a). A nanoshell of silver then is grown over the nanocore material. Silver nanoparticles have the absorbance spectrum typical of that shown in FIG. 5; additional Mie theory calculations allow design for maximum spectral overlap (FRET) between core and shell. The nanoparticle is then coated with polyethylene glycol (PEG), to which the A33 antibody is attached. The nanomaterial is further processed for intravenous administration into a patient with colorectal adenocarcinoma and/or inoperable liver metastases.

After administration of the nanoparticles, sufficient to allow targeting to the diseased cells, the patient is prepared for a PET-CT x-ray scan. PET is used initially and at the completion of treatment to identify active cancer cells (or lack thereof). The CT irradiation scheme is optimized based on several factors, including 1) the nanoparticles being used, 2) the organ or body region being treated (here, the liver), 3) the disease being treated (here colon cancer) and 4) the size and physical condition of the patient and extent of disease. Large numbers of cancer cells (for example, either large tumors or many tumors in the liver), if killed rapidly, may overload the body's ability to eliminate dead tissue, creating toxic health-threatening conditions. In such cases, the overall CENT treatment plan, and the accompanying specific irradiation regime, must be optimized for the patient, requiring a series of treatments of lower dosage CENT particles and less intense (and more regionally limited in the body) ionizing radiation.

At the other extreme of disease (other than adjuvant therapy), for example, one inoperable but small tumor (sphere less than 1 cm in diameter), may not require a patient optimized treatment protocol; if the tumor is heat-responsive, only the irradiation protocol of a conventional CT scan of the liver (~1010 80 KeV-photons per cm²) and a dose of CENT particles sufficient for such tumor size, may constitute the first CT treatment. Regionally-focused diagnostic PET scans, before and after treatment, determine the efficacy of the first CENT-CT treatment. If several exposures of x-ray radiation are to be necessary to generate the required therapeutic heating, the maximum safe dose to the patient determines the appropriate regimen.

In the case of extensive metastatic liver disease and a weakened patient (for example, having abnormal function of liver or kidney), the patient must undergo a set of calibration treatments to determine the optimized therapeutic treatment. The first calibration treatment involves only a limited dose of CENT-particles and radiation to kill the tumor mass that medical experts believe the weakened patient may safely tolerate, even though active tumor will still remain. The frequency and optimization of all aspects of additional treatment are patient-dependent in such cases.

Cancer cells from a tumor biopsy may be subjected to in vitro testing to determine both the likely response to a CENT treatment and help the design and optimization of the irradiation regime for efficacy in the specific patient.

Thermotherapy may be considered either as the primary treatment or as an adjuvant therapy in combination with surgery, chemotherapy or radiation.

Modifications and variations of the methods and reagents described herein will be obvious to those skilled in the art from the foregoing detailed description and are intended to come within the scope of the appended claims. All references are specifically incorporated herein, to the extent required.

I claim:

1. A method for generating heat in an amount sufficient to kill or damage target cells or tissue, comprising:
    a) delivering on, in or nearby cells or tissue to be killed or damaged, nanoparticles comprising a core of a first chemical composition surrounded by a shell of a second chemical composition, wherein the core comprises core-exciting energy absorbing species which transfer energy to the shell in an amount sufficient for the shell to heat the cells or tissue to be killed or damaged, when the nanoparticles are exposed to core-exciting energy, and
    b) exposing the nanoparticles to the core-exciting energy in a manner and duration such that the nanoparticles emit heat in sufficient quantity to kill or damage the cells or tissue.

2. The method of claim 1, wherein the nanoparticles are nanoshells or nanorods.

3. The method of claim 1, wherein the core exciting energy absorbing species transfer energy to the shell by emitting electromagnetic radiation in the range of 100 nanometers (nm) to 6000 nm, which is then absorbed by the shell and converted to heat.

4. The method of claim 1, wherein the core-exciting energy absorbing species emit radiation which, over the duration of time and with decay in luminosity, produces a total radiation energy of at least 100 electron volts (eV) with frequencies that fall within the absorbance band spectrum of the shell.

5. The method of claim 1, wherein the core-exciting energy is electromagnetic radiation with a wavelength ranging from 10 nm to 0.0001 nm.

6. The method of claim 5, wherein the core-exciting energy is x-ray or gamma radiation which is generated by a computed-tomography (CT) scanner, an x-ray or gamma-ray machine that is used in medicine, dentistry or imaging, or an x-ray laser.

7. The method of claim 1, wherein the nanoparticles have an average length or average diameter less than 1000 nm.

8. The method of claim 1, wherein the core-exciting energy absorbing species transfer energy to the shell by x-ray excited luminescence or x-ray excited persistent phosphorescence.

9. The method of claim 1, wherein the shell comprises gold, silver, platinum, palladium, or mixtures thereof.

10. The method of claim 1, wherein the shell comprises a material that allows external x-rays or gamma-rays to reach the core-exciting energy absorbing species in sufficient quantity to excite the core-exciting energy absorbing species, and then absorbs energy from the core-exciting energy absorbing species, and converts the energy to heat.

11. The method of claim 1, wherein, after the exposure to external core-exciting energy has been terminated, the core-exciting energy absorbing species transfer energy to the shell by emitting electromagnetic radiation, in the wavelength range of 100 nm to 6000 nm, for a duration longer than one second.

12. The method of claim 11, wherein the core-exciting energy is one of a pulse of core-exciting energy that is less than one second in duration, a series of radiation pulses administered over a period of time, or a continuous exposure of radiation for a period of time.

13. The method of claim 1, wherein the shell comprises a material capable of absorbing x-ray or gamma-ray radiation.

14. The method of claim 1, wherein the core-exciting energy absorbing species is selected from the group consisting of
   forms of strontium aluminate, $Sr_aAl_bO_c$, where a, b and c are integers that may vary;
   forms of strontium aluminate doped with a rare earth element (RaE), $Sr_aAl_bO_c$:RaE, wherein a, b and c are integers that may vary and RaE=La, Lu, Ce, Pr, Nd, Sm, Eu, Tb, Dy, Ho, Er, Tm, or Yb in one or more oxidation states;
   forms of strontium aluminate co-doped with two or more different rare earth elements (RaEs), $Sr_aAl_bO_c$:(RaE)$_2$, wherein a, b and c are integers that may vary and RaE=La, Lu, Ce, Pr, Nd, Sm, Eu, Tb, Dy, Ho, Er, Tm, or Yb in one or more oxidation states;
   forms of rare-earth ion-doped gadolinium oxide or oxysulfide phosphor, $Gd_2O_3$:RaE$^{3+}$ or $Gd_2O_2S$:RaE$^{3+}$, wherein RaE=La, Lu, Ce, Pr, Nd, Sm, Eu, Tb, Dy, Ho, Er, Tm, or Yb;
   rare-earth (RaE) ion co-doped alkaline earth aluminates, $xMO+yAl_2O_3$: RaE' RaE, where x and y are integers, and M=Ca, Sr, or Ba, and RaE=La, Lu, Ce, Pr, Nd, Sm, Eu, Tb, Dy, Ho, Er, Tm, or Yb;
   rare-earth- or transition-metal-doped metal halides;
   CdS, CdSe, CdTe, $CaWO_4$, ZnS:Cu, TmO, ZnSe:Te, ZnS, ZnO, $TiO_2$, GaN, GaAs, GaP, InAs, InP, $Y_2O_3$, $WO_3$, and $ZrO_2$.

15. The method of claim 1, wherein the core-exciting energy absorbing species absorb energy, then emit electromagnetic radiation as a result of a dopant ion that is an activator of luminescence.

16. The method of claim 1, wherein the core-exciting energy absorbing species comprise a material doped with at least one rare-earth- or lanthanide-series element of the periodic table in an amount greater than 0.1 mass percent.

17. The method of claim 1, wherein the nanoparticles have targeting molecules bound thereto.

18. The method of claim 1, wherein the nanoparticles have one or more heat-catalyzed functionalized agents bound to, or in a kit for administration with, the nanoparticles.

19. The method of claim 1, further comprising administering the nanoparticles to kill undesirable tissue that has arisen due to transformation; adipose tissue; plaques present in vascular tissue and overproliferation; birthmarks and other vascular lesions of the skin; scars and adhesions; or irregularities in connective tissue or bone.

20. The method of claim 1, further comprising administering the nanoparticles to kill infected or inflamed cells or tissue.

21. The method of claim 1, further comprising administering the nanoparticles to kill transformed or cancerous cells or tissue.

22. The method of claim 1, further comprising administering the nanoparticles and a separate contrast agent or diagnostic marker to the targeted tissue or cells for the purpose of monitoring the condition of the targeted cell or material.

23. The method of claim 1, further comprising removing nanoparticles from the cells or tissues.

24. The method of claim 7, wherein the nanoparticles have an average length or average diameter of less than 500 nm.

25. The method of claim 24, wherein the nanoparticles have an average length or average diameter of less than 300 nm.

26. The method of claim 14, wherein the core-exciting energy absorbing species is selected from the group consisting of $Sr_4Al_{14}O_{25}$; $SrAl_2O_4$; $SrAl_2O_7$; $Sr_3Al_2O_6$; Europium(II)-doped $Sr_4Al_{14}O_{25}$, $SrAl_2O_4$, $SrAl_2O_7$, or $Sr_3Al_2O_6$; Dysprosium(III)-doped $Sr_4Al_{14}O_{25}$, $SrAl_2O_4$, $SrAl_2O_7$, or $Sr_3Al_2O_6$; Neodymium(III)-doped $Sr_4Al_{14}O_{25}$, $SrAl_2O_4$, $SrAl_2O_7$, or $Sr_3Al_2O_6$; $Sr_4Al_{14}O_{25}$:Eu$^{2+}$:Dy$^{3+}$; $SrAl_2O_4$:Eu$^{2+}$:Dy$^{3+}$; $SrAl_2O_7$:Eu$^{2+}$:Dy$^{3+}$; $Sr_3Al_2O_6$:Eu$^{2+}$:Dy$^{3+}$; $Sr_4Al_{14}O_{25}$:Eu$^{2+}$:Nd$^{3+}$; $SrAl_2O_4$:Eu$^{2+}$:Nd$^{3+}$; $SrAl_2O_7$:Eu$^{2+}$:Nd$^{3+}$; $Sr_3Al_2O_6$:Eu$^{2+}$:Nd$^{3+}$; $LaF_3$:Ce$^{3+}$; $LuF_3$:Ce$^{3+}$ $CaF_2$:Mn$^{2+}$, $CaF_2$:Eu$^{2+}$, $BaFBr$:Eu$^{2+}$, $BaFBr$:Mn$^{2+}$, $CaPO_4$:Mn$^{2+}$, $LuI_3$:Ce, $SrI_2$:Eu, $CaI_2$:Eu, and $GdI_3$:Ce.

27. Nanoparticles for generating heat in an amount sufficient to kill or damage target cells or tissue, comprising a core of a first chemical composition surrounded by a shell of a second chemical composition, wherein the core comprises core-exciting energy absorbing species which transfer energy to the shell in an amount sufficient for the shell to heat the cells or tissue to be killed or damaged, when the nanoparticles are exposed to core-exciting energy.

28. The nanoparticles of claim 27, wherein the nanoparticles are nanoshells or nanorods.

29. The nanoparticles of claim 27, wherein the core-exciting energy absorbing species transfer energy to the shell by emitting electromagnetic radiation in the range of 100 nm to 6000 nm, which is then absorbed by the shell and converted to heat.

30. The nanoparticles of claim 27, further comprising core-exciting energy absorbing species attached to the nanoparticle surface.

31. The nanoparticles of claim 27, wherein the core-exciting energy is electromagnetic radiation with a wavelength ranging from 10 nm to 0.0001 nm.

32. The nanoparticles of claim 27, wherein the core-exciting energy x-ray or gamma radiation which is generated by a computed-tomography (CT) scanner, an x-ray or gamma-ray machine that is used in medicine, dentistry or imaging, or an x-ray laser.

33. The nanoparticles of claim 27, wherein the nanoparticles have an average length or average diameter less than 1000 nm.

34. The nanoparticles of claim 27, wherein the core-exciting energy absorbing species transfer energy to the shell by x-ray excited luminescence or x-ray excited persistent phosphorescence.

35. The nanoparticles of claim 27, wherein the shell comprises gold, silver, platinum, palladium, or mixtures thereof.

36. The nanoparticles of claim 27, wherein the shell comprises a material that allows external x-rays or gamma-rays to reach the core-exciting energy absorbing species in sufficient quantity to excite the core-exciting energy absorbing species, and then absorbs energy from the core-exciting energy absorbing species, and converts the energy to heat.

37. The nanoparticles of claim 27, wherein, after the exposure to external core-exciting energy has been terminated, the core-exciting energy absorbing species transfer energy to the shell by emitting electromagnetic radiation, in the wavelength range of 100 nm to 6000 nm, for a duration longer than one second.

38. The nanoparticles of claim 27, wherein the shell comprises a material capable of x-ray-excitable luminescence or x-ray-excitable persistent phosphorescence.

39. The nanoparticles of claim 27, wherein the core-exciting energy absorbing species is selected from the group consisting of
forms of strontium aluminate, $Sr_aAl_bO_c$, where a, b and e are integers that may vary;
forms of strontium aluminate doped with a rare earth element (RaE), $Sr_aAl_bO_c$:RaE, wherein a, b and c are integers that may vary and RaE=La, Lu, Ce, Pr, Nd, Sm, Eu, Tb, Dy, Ho, Er, Tm, or Yb in one or more oxidation states;
forms of strontium aluminate co-doped with two or more different rare earth elements (RaEs), $Sr_aAl_bO_c$:(RaE)$_2$, wherein a, b and c are integers that may vary and RaE=La, Lu, Ce, Pr, Nd, Sm, Eu, Tb, Dy, Ho, Er, Tm, or Yb in one or more oxidation states;
forms of rare-earth ion-doped gadolinium oxide or oxysulfide phosphor, $Gd_2O_3$:RaE$^{3+}$ or $Gd_2O_2S$:RaE$^{3+}$, wherein RaE=La, Lu, Ce, Pr, Nd, Sm, Eu, Tb, Dy, Ho, Er, Tm, or Yb;
rare-earth (RaE) ion co-doped alkaline earth aluminates, xMO+y$Al_2O_2$:RaE' RaE, where x and y are integers, and M=Ca, Sr, or Ba, and RaE=La, Lu, Ce, Pr, Nd, Sm, Eu, Tb, Dy, Ho, Er, Tm, or Yb;
rare-earth- or transition-metal-doped metal halides;
CdS, CdSe, CdTe, $CaWO_4$, ZnS:Cu, TmO, ZnSe:Te, ZnS, ZnO, $TiO_2$, GaN, GaAs, GaP, InAs, InP, $Y_2O_3$, $WO_3$, and $ZrO_2$.

40. The nanoparticles of claim 27, wherein the core-exciting energy absorbing species absorb energy, then emit electromagnetic radiation as a result of a dopant ion that is an activator of luminescence.

41. The nanoparticles of claim 27, wherein the core-exciting energy absorbing species comprise a material doped with at least one rare-earth- or lanthanide-series element of the periodic table in an amount greater than 0.1 mass percent.

42. The nanoparticles of claim 27, wherein the nanoparticles have targeting molecules bound thereto.

43. The nanoparticles of claim 27, wherein the nanoparticles have one or more heat-catalyzed functionalized agents bound thereto.

44. The nanoparticles of claim 27, wherein the shell comprises a material sufficiently transparent to external x-rays or gamma-rays to allow the rays to reach the core-exciting energy absorbing species in sufficient quantity to excite the core-exciting energy absorbing species, which then emit energy in sufficient type and amount to heat to the surrounding shell; and wherein the nanoparticles further comprise a core-shell binder between the core and shell.

45. The nanoparticles of claim 44, wherein the core-shell binder facilitates binding an ionic lattice to a metal, and does not cause detriment to energy flow between the core and shell.

46. The nanoparticles of claim 45, wherein the core-shell binder is selected from the group consisting of phosphates and amines.

47. The nanoparticles of claim 27, further comprising one or more stabilizing materials on or within the core.

48. The nanoparticles of claim 27, wherein the core-exciting energy absorbing species emit radiation which, over the duration of time and with decay in luminosity, produces a total radiation energy of at least 100 electron volts (eV) with frequencies that fall within the absorbance band spectrum of the shell.

49. The nanoparticles of claim 33, wherein the nanoparticles have an average length or average diameter of less than 500 nm.

50. The nanoparticles of claim 49, wherein the nanoparticles have an average length or average diameter of less than 300 nm.

51. The nanoparticles of claim 39, wherein the core-exciting energy absorbing species is selected from the group consisting of $Sr_4Al_{14}O_{25}$; $SrAl_2O_4$; $SrAl_2O_7$; $Sr_3Al_2O_6$; Europium(II)-doped $Sr_4Al_{14}O_{25}$, $SrAl_2O_4$, $SrAl_2O_7$, or $Sr_3Al_2O_6$; Dysprosium(III)-doped $Sr_4Al_{14}O_{25}$, $SrAl_2O_4$, $SrAl_2O_7$, or $Sr_3Al_2O_6$; Neodymium(III)-doped $Sr_4Al_{14}O_{25}$, $SrAl_2O_4$, $SrAl_2O_7$, or $Sr_3Al_2O_6$; $Sr_4Al_{14}O_{25}$:Eu$^{2+}$:Dy$^{3+}$; $SrAl_2O_4$:Eu$^{2+}$:Dy$^{3+}$; $SrAl_2O_7$:Eu$^{2+}$:Dy$^{3+}$; $Sr_3Al_2O_6$:Eu$^{2+}$:Dy$^{3+}$; $Sr_4Al_{14}O_{25}$:Eu$^{2+}$:Nd$^{3+}$; $SrAl_2O_4$:Eu$^{2+}$:Nd$^{3+}$; $SrAl_2O_7$:Eu$^{2+}$ Nd$^{3+}$; $Sr_3Al_2O_6$:Eu$^{2+}$: Nd$^{3+}$; $LaF_3$:Ce$^{3+}$; $LuF_3$:Ce$^{3+}$ $CaF_2$:Mn$^{2+}$, $CaF_2$:Eu$^{2+}$, BaFBr:Eu$^{2+}$, BaFBr:Mn$^{2+}$, $CaPO_4$: Mn$^{2+}$, $LuI_3$:Ce, $SrI_2$:Eu, $CaI_2$:Eu, and $GdI_3$:Ce.

* * * * *

UNITED STATES PATENT AND TRADEMARK OFFICE
CERTIFICATE OF CORRECTION

PATENT NO. : 8,197,471 B1
APPLICATION NO. : 13/052951
DATED : June 12, 2012
INVENTOR(S) : Samuel Harry Tersigni Page 1 of 1

It is certified that error appears in the above-identified patent and that said Letters Patent is hereby corrected as shown below:

Claim 14, column 21, line 51, replace "halides;" with --halides--.
Claim 14, column 21, line 53, replace "InP,$Y_2O_3$" with --InP, $Y_2O_3$--.
Claim 39, column 23, line 24, replace "where a, b and e" with --where a, b and c--.

Signed and Sealed this
Eleventh Day of September, 2012

David J. Kappos
*Director of the United States Patent and Trademark Office*